Figure 1:
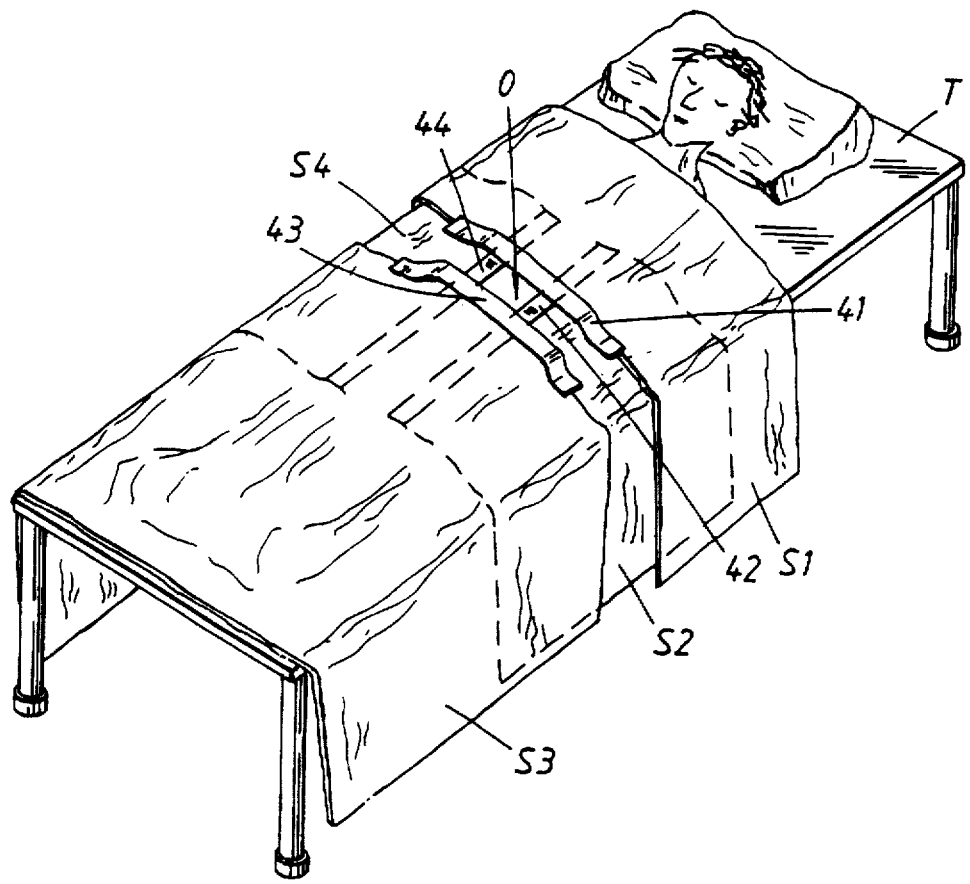

United States Patent [19]
Löfgren et al.

[11] Patent Number: 5,778,890
[45] Date of Patent: Jul. 14, 1998

[54] SURGICAL DRAPE HAVING ADHESIVE MARGINS

[75] Inventors: Kristina Löfgren, Mölnlycke; Ewa Kölby Falck, Göteborg; Bengt Netsner, Lindome, all of Sweden

[73] Assignee: Mölnlycke AB, Gothenburg, Sweden

[21] Appl. No.: 913,884
[22] PCT Filed: Mar. 27, 1996
[86] PCT No.: PCT/SE96/00398
§ 371 Date: Sep. 24, 1997
§ 102(e) Date: Sep. 24, 1997
[87] PCT Pub. No.: WO96/29949
PCT Pub. Date: Oct. 3, 1996

[30] Foreign Application Priority Data

Mar. 30, 1995 [SE] Sweden .................................. 9501157

[51] Int. Cl.$^6$ .................................................... A61B 19/00
[52] U.S. Cl. .................................................... 128/849; 128/853
[58] Field of Search .................................... 128/849–856

[56] References Cited

U.S. PATENT DOCUMENTS

| 3,263,680 | 8/1966 | Morgan | 128/853 |
|---|---|---|---|
| 3,561,439 | 2/1971 | Bayer | 128/853 |
| 4,316,455 | 2/1982 | Stoneback | 128/853 |
| 4,316,456 | 2/1982 | Stoneback | 128/853 |
| 5,546,960 | 8/1996 | Billgren | 128/849 |

FOREIGN PATENT DOCUMENTS 0 619 099   10/1994   European Pat. Off. .
449 433     5/1987    Sweden .

Primary Examiner—Michael A. Brown
Attorney, Agent, or Firm—Young & Thompson

[57] ABSTRACT

The present invention relates to a surgical drape having an adhesive edge or border and including a liquid-impermeable layer and a layer of absorbent material fastened thereto. According to the present invention, at least one edge or border of the surgical drape has affixed thereto a separate edge-piece which includes an adhesive coating on that side which in use lies proximal to the patient's body.

10 Claims, 1 Drawing Sheet

SURGICAL DRAPE HAVING ADHESIVE MARGINS

The present invention relates to a surgical drape having a self-adhesive edge or border and comprising a liquid-impervious layer and a layer of absorbent material fastened thereto.

In many surgical operations, the surgical or wound area is screened with the aid of a plurality of surgical drapes, dressing towels or the like which are placed on the patient around the surgical area and there fastened to the patient's skin along those edges of the drapes that face towards the surgical area. In order to facilitate application of the surgical drapes around the surgical area, the drapes are often provided with an adhesive coating on the underside of one edge of the drape. One problem with known surgical drapes of the kind defined in the introduction where the absorbent material is comprised of nonwoven material laminated on a plastic layer resides in the danger of the adhesive bond loosening at mutually overlapping edge parts of adjacent drapes. Another problem is that the properties of said edges are fully dependent on the properties of the material from which the surgical drape is comprised and do not therefore always have properties that are optimal for the application in question. The provision of an adhesive coating along the edges or borders of such surgical drapes also complicates their manufacture.

An object of the present invention is to avoid these problems.

This object is achieved in accordance with the invention with a surgical drape of the aforedefined kind which is characterized in that at least one edge of the drape includes a separate edge-piece which is attached to the drape itself and which includes an adhesive coating on that side which in use lies proximal to a patient's body. Because thee edge-piece comprises a part which is separate from the drape in general, the material from which the edge-piece is made can be chosen in full accord with the properties desired of said edge-piece while, at the same time, enabling the surgical drape in general, ie the drape itself, to be optimized independently of said edge-part. Furthermore, the risk of adhesive bonds between overlapping parts of the edge-pieces of mutually adjacent surgical drapes loosening while in use can be eliminated by suitable selection of edge-piece material and adhesive coating. Furthermore, the process of applying an adhesive coating to the drape edge-piece is separate from the manufacture of the drape itself, which simplifies the manufacture of the drape in comparison with the manufacture of known drapes of the aforedefined kind and renders such manufacture less expensive.

In one preferred embodiment, the separate edge-piece extends along the full length of the drape edge with which it is to coact, and the separate edge-piece is produced from a plastic material. The edge-piece is also stiffer in its transverse direction than in its longitudinal direction and is fastened to the surgical drape itself on that side thereof which in use lies distal from a patient. The edge-pieces are preferably glued or welded to the surgical drape.

In one variant, the edge-piece is attached to the surgical drape on that side of the drape which in use lies proximal to a patient.

In another variant, the separate edge-piece is manufactured from vapour permeable material.

By surgical drape is meant here drapes of all sizes and thus also includes dressing towels, abdominal sheets, plain sheets, slit sheets, etc..

Figure 2:
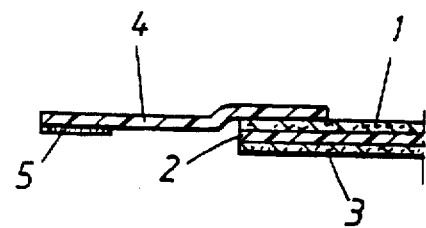

The invention will now be described with reference to the accompanying drawings, in which FIG. 1 is a schematic perspective view of a patient lying on an operating table with the surgical area, or wound area, screened with the aid of four surgical drapes constructed in accordance with one embodiment of the invention; and FIG. 2 is a sectional view taken transversely to the longitudinal direction of one edge or border of a surgical drape in FIG. 1.

FIG. 1 shows a patient lying on an operating table T where a rectangular surgical area O has been screened with the aid of four surgical drapes S1–S4. As shown in FIG. 2, each of these drapes S1–S4 is comprised of a laminate which includes an upper layer 1 of absorbent material, for instance nonwoven material, an intermediate plastic layer 2, and a bottom layer 3 of soft material, for instance a wadding-like material. An edge-piece 4 is attached in some suitable way, e.g. glued or welded, to that edge of the laminate 1–3 which faces towards the surgical area O. Each edge-piece 4 extends along at least a part of said edge or border of the laminate 1–3 and part of the edge-piece 4 extends outwardly beyond the edge of the laminate. A bead or string 5 of adhesive is applied to the underside of the free longitudinal side edge of said edgepiece. The longitudinal directions of the edge-pieces are defined as directions parallel with the edges of the laminate 1–3 of the drapes S1–S4 to which respective edge-pieces are attached. The edge-pieces of the drapes S1–S4 in FIG. 1 are reference 41, 42, 43 and 44 respectively.

The edge-pieces will preferably be made of a fluff-free material, so as to ensure that no parts of the material will loosen and fall down into the surgical or wound area. The material will also preferably be hydrophobic, or will have been made hydrophobic, so as to prevent liquid from being absorbed from a surgical wound and to eliminate the risk of the adhesive bond loosening between mutually overlapping parts of respective edge-pieces 41–44. It is also important that the edge-pieces are able to conform to or follow the contours of the patient's body, and the material from which the edge-pieces are made will be highly flexible about transverse axes and preferably also elastic. An advantage is gained from a handling aspect when the edge-piece material is relatively flexurally rigid about longitudinal axes. These advantages are conveniently fulfilled when the edge-pieces are made from a plastic material. Hydrophobized nonwoven material or material comprised of several layers of different kinds may also be used.

In order to reduce the risk of skin irritation or other skin reactions, the edge-pieces may be comprised of vapour permeable plastic film, so-called breathable plastic. The adhesive coating will preferably consist of a skin-friendly adhesive and may be a continuous or an intermittent coating. The edge-pieces may be either opaque or transparent and their widths may vary in accordance with the type of sergery for which the surgical drape is to be used. The width of the adhesive bead or string may also vary as necessary and as desired.

As before mentioned, the edge-pieces may extent fully or partially along one edge or border of the surgical drape. The edge-pieces 42, 44 illustrated in FIG. 1 extend along the full length of one edge of the surgical drape S2 and S4 respectively, whereas the edge-pieces 41, 43 extend only along a central part of respective drapes S1 and S3.

Prior to folding the surgical drape and sterile-packaging the drape subsequent to its manufacture, the adhesive beads are covered with release paper and the edge-pieces may optionally be folded in over the upper edge of the drape in conjunction with folding the package, so as to facilitate application in use.

It will be understood that the illustrated and described embodiment of the surgical drape can be modified in many ways within the scope of the invention. For instance, the edge-pieces may be fastened to the underside of the drape itself instead of to its upper side, as in the case of FIG. 1. Furthermore, the drape laminate may have a construction different to that described, for instance it may include an absorbent material other than nonwoven material or may comprise two layers instead of three. The edge-pieces may, of course, be affixed along more than one edge of the drape laminate. For instance, when the drape is a slit surgical sheet, edge-pieces may be affixed to both edges of the slit. The invention is therefore restricted solely by the content of the following Claims.

We claim:

1. A surgical drape (S1–S4) having an adhesive edge and including a liquid-impermeable layer (2) and a layer of absorbent material (1) fastened thereto, characterized in that at least one edge or border of the drape (S1–S4) includes a separate edge-piece (41–44) which is fastened to the composite layers constituting the drape itself with a part of the edge-piece extending outwardly beyond said edge of the drape itself and which includes an adhesive coating (5) on that side which lies proximal to the patient's body in use.

2. A surgical drape according to claim 1, characterized in that the separate edge-piece (42, 44) extends along the full length of the drape edge concerned.

3. A surgical drape according to claim 1, characterized in that the separate edge-piece (41, 43) extends solely along a part of the drape edge concerned.

4. A surgical drape according to claim 1, characterized in that the separate edge-piece (41–44) is made of a plastic material.

5. A surgical drape according to claim 4, characterized in that the edge-piece (41–44) is more rigid in its transverse direction than in its longitudinal direction.

6. A surgical drape according to claim 1, characterized in that the separate edge-piece is made of vapour permeable material.

7. A surgical drape according to claim 1, characterized in that the edge-piece (41–44) is fastened to the surgical drape on that side of the drape (S1–S4) which in use lies distal from a patient.

8. A surgical drape according to claim 1, characterized in that the edge-piece is fastened to the surgical drape on that side of the drape which in use lies proximal to a patient.

9. A surgical drape according to claim 1, characterized in that the edge-piece is glued or welded to the surgical drape.

10. A surgical drape according to claim 1, characterized in that the edge-piece is comprised of multi-layer material.

* * * * *